United States Patent

Kisuno et al.

[11] Patent Number: 5,889,088
[45] Date of Patent: Mar. 30, 1999

[54] COMPOSITE PARTICLE AQUEOUS SUSPENSION AND PROCESS FOR PRODUCING SAME

[75] Inventors: Atsushi Kisuno; Tatsuo Ansai, both of Tsukuba; Shihoko Aizawa, Kitasoma-gun, all of Japan

[73] Assignee: Hodogaya Chemical Co., Ltd., Kawasaki-sho, Japan

[21] Appl. No.: 796,180

[22] Filed: Feb. 7, 1997

[30] Foreign Application Priority Data

Feb. 9, 1996 [JP] Japan ................................ 8-024208

[51] Int. Cl.$^6$ ........................................ C08K 9/04
[52] U.S. Cl. ..................... 523/205; 424/489; 424/497; 428/405; 428/407; 514/937; 514/975; 523/207; 523/209
[58] Field of Search ..................... 424/489, 497; 428/405, 407; 514/937, 975; 523/205, 206, 207, 208, 209

[56] References Cited

U.S. PATENT DOCUMENTS

| | | | |
|---|---|---|---|
| 3,779,981 | 12/1973 | Ward | 523/206 |
| 3,914,192 | 10/1975 | Flautt | 523/207 |
| 4,369,264 | 1/1983 | Baumann | 523/209 |
| 4,420,512 | 12/1983 | Ogawa | 523/205 |
| 4,916,171 | 4/1990 | Brown | 523/206 |
| 4,965,007 | 10/1990 | Yudelson | 428/407 |
| 5,140,071 | 8/1992 | Kroker | 523/209 |
| 5,278,203 | 1/1994 | Harms | 523/205 |
| 5,393,461 | 2/1995 | Fillipova | 252/314 |
| 5,534,585 | 7/1996 | Roulstone | 523/205 |
| 5,597,551 | 1/1997 | Malawer | 424/47 |
| 5,643,974 | 7/1997 | Simpson | 523/203 |

FOREIGN PATENT DOCUMENTS

| | | |
|---|---|---|
| 482417 | 4/1992 | European Pat. Off. . |
| 46-20519 | 6/1971 | Japan . |
| 52-66633 | 6/1977 | Japan . |
| 57-58601 | 4/1982 | Japan . |
| 5-201801 | 8/1983 | Japan . |
| 58-162504 | 9/1983 | Japan . |
| 61-63601 | 4/1986 | Japan . |
| 61-97202 | 5/1986 | Japan . |
| 62-45501 | 2/1987 | Japan . |
| 63-107901 | 5/1988 | Japan . |
| 2-111703 | 4/1990 | Japan . |
| 6-9302 | 1/1994 | Japan . |
| 6-316502 | 11/1994 | Japan . |
| 7-157401 | 6/1995 | Japan . |
| 2026341 | 2/1980 | United Kingdom . |
| 2128089 | 4/1984 | United Kingdom . |

*Primary Examiner*—Paul R. Michl
*Attorney, Agent, or Firm*—IP Group Of Pillsbury Madison & Sutro, LLP

[57] ABSTRACT

A stable aqueous suspension of composite particles each including a core formed from a solid or liquid particle and a coating layer formed on the core particle and including at least one high molecular weight surfactant compound having an average molecular weight of 1100 or more and at least one low molecular weight surfactant compound having an average molecular weight of 1100 or less and at least 400 below the average molecular weight of the high molecular weight surfactant compound and optionally a suspension stabilizer, is produced by subjecting a particulate solid substance or a liquid substance to a suspending treatment in an aqueous medium containing the above-mentioned high and low molecular weight surfactant compounds, and optionally the suspension stabilizer.

22 Claims, No Drawings

5,889,088

COMPOSITE PARTICLE AQUEOUS SUSPENSION AND PROCESS FOR PRODUCING SAME

BACKGROUND OF THE INVENTION (1) Field of the Invention

The present invention relates to an aqueous suspension of composite particles and a process for producing the same. More particularly, the present invention relates to a suspension of composite particles containing core solid particles or core liquid droplets in an aqueous medium in which the solid particles or liquid droplets-containing composite particles are suspended with a high storage stability, and even when the composite particles are precipitated, they can be easily re-suspended, and a process for producing the same.

(2) Description of the Related Art

It is known that an aqueous suspension of solid particles, for example, particulate agricultural chemicals, or liquid droplets, for example, an oil, can be prepared by the following methods.

For example, Japanese Examined Patent Publication No. 46-20,519 discloses a method in which a hydrophobic agricultural chemical is wet-pulverized in water or a hydrophilic medium and the resultant hydrophilicized fine particles are suspended in the medium. Japanese Examined Patent Publication No. 58-2,440 discloses an aqueous suspension of an agricultural chemical comprising a solid agricultural chemical having a poor solubility in water or a combination of a solid agricultural chemical having a poor solubility in water with a water-soluble solid agricultural chemical; a surfactant, a water-soluble high molecular compound and water, and having a viscosity of 200 to 500 cP at a temperature of 20° C.

Japanese Unexamined Patent Publication No. 57-58,601 discloses a suspension agricultural chemical comprising an agricultural chemical insoluble or scant soluble in water or organic solvents, a surfactant, a xanthane gum and water.

Japanese Unexamined Patent Publication No. 2-111,703 discloses a suspended agricultural chemical comprising a water-insoluble or scant soluble agricultural chemical, a surfactant, a water-soluble biopolymer and water.

Japanese Examined Patent Publication Nos. 7-47,521, 7-47,522, 64-7,041, 63-58,802, and 6-78,202 disclose aqueous suspension agricultural chemicals comprising a herbicide or biocide chemical and a surfactant.

Japanese Unexamined Patent Publications No. 5-201,801, No. 6-9,302 and No. 7-157,401 disclose an aqueous suspension agricultural chemical comprising a herbicide-active component or an other agricultural chemical component and a surfactant, and at least one member selected from thickeners, salts, clay minerals and metal oxide gels.

Japanese Unexamined Patent Publication No. 58-162,504 discloses an aqueous herbicide emulsion containing a liquid herbicide and a surfactant.

Japanese Unexamined Patent Publication No. 6-316,502 discloses a method of suspending a water stint soluble, solid, physiologically active substance in a liquid medium containing a nonionic surfactant having an HLB of 1 to 9 and a nonionic surfactant having an HLB of 10 to 20, the liquid medium optionally containing a clay mineral such as bentonite.

It is also known that where an aqueous suspension of solid or liquid particles is prepared, the storage stability of the aqueous suspension is variable depending on the average particle size of the particles. Also, it is believed that unless the substance to be suspended is divided to an extent such that the resultant average particle size is in the range of from 0.5 to 5 $\mu$m, it is difficult to stably suspend the pulverized substance particles in a suspension medium. Therefore, to enhance the stability of the particle suspension, the substance must be finely pulverized, and thus for the fine pulverization, a specific pulverizing machine, for example, Dyno mill, air mill, hammer mill, tower mill, vibration mill or sand mill must be employed. This necessity causes the suspension cost to be high. Also, the higher the content of the particles in the suspension, the higher the viscosity of the suspension. Therefore, an aqueous suspension of fine particles having an average particle size of 0.5 to 5 $\mu$m exhibits a high viscosity and thus is difficult to practically use the suspension. Namely, in the preparation of a suspension of solid or liquid particles which are insoluble or stint soluble in water, practically there is an upper limit to the content of the particles. Further, since the finely divided solid or liquid particles have a large surface area and thus the dissolution rate in water or hydrolysis rate increases, the suspension stability of the particles decreases in response to an increase in the surface area of the particles. Accordingly, in the conventional technique, an aqueous suspension of the solid or liquid particles capable of satisfying all of the requirements of high dispersion stability over a long period, high restriction of hydrolysis of the particles and a high re-suspending property of the particles has not yet been obtained.

Further, in fields of pigments, medicines, cosmetics, dyestuffs, paints and building materials which may be solid or liquid, when they are used in the state of a suspension in an aqueous medium, or the aqueous suspension is used as a starting material, it is strongly required that the aqueous suspension exhibits a high storage stability over a long time and even where a portion of the particles is precipitated during long time storage, the precipitated particle portion can be easily re-suspended. However, the aqueous suspension capable of satisfying all of the requirement has not yet been obtained.

SUMMARY OF THE INVENTION

An object of the present invention is to provide an aqueous suspension of solid or liquid particles, which suspension exhibits a high suspension stability, a high resistance to dissolution and hydrolysis and an excellent capability of re-suspending, and a process for producing the solid or liquid particle aqueous suspension easily and at a low cost.

The above-mentioned object can be attained by the aqueous suspension and the process for producing the same of the present invention.

The aqueous suspension of composite particles of the present invention comprises (A) an aqueous suspension medium, and (B) a plurality of composite particles suspended in the aqueous suspension medium, each of the composite particles comprising:

(a) a core consisting of a solid or liquid particle, and (b) a coating layer formed on the peripheral surface of the core particle and comprising (i) a high molecular weight surfactant component comprising at least one high molecular weight surfactant compound having an average molecular weight of 1100 or more and, (ii) a low molecular weight surfactant component comprising at least one low molecular weight surfactant compound having an average molecular weight of 1100 or less and at least 400 below the average molecular weight of the high molecular weight surfactant compound.

In the aqueous suspension of the present invention, preferably the core particles have an average particle size of 3 to 500 μm, and the composite particles have an average particle size of 6 to 1,000 μm.

The process of the present invention for producing the aqueous composite particle suspension comprises the step of subjecting a particulate solid substance or a liquid substance to a suspending treatment in an aqueous treating liquid comprising an aqueous suspension medium, a high molecular weight surfactant component comprising at least one high molecular weight surfactant compound having an average molecular weight of 1100 or more, and a low molecular weight surfactant component comprising at least one low molecular weight surfactant compound having an average molecular weight of 1100 or less and of at least 400 below the average molecular weight of the high molecular weight surfactant compound, thereby to provide a plurality of solid or liquid particles suspended in the aqueous suspension medium and each comprising a core consisting of the solid or liquid particle, and a coating layer formed on the peripheral surface of the core particle and comprising the high molecular weight surfactant component and the low molecular weight surfactant component.

Preferably, the aqueous composite particle suspension of the present invention comprises 0.1 to 75% by weight of the solid or liquid core particles, 0.1 to 5% by weight of the high molecular surfactant compound and 0.1 to 25% by weight of the low molecular weight surfactant compound.

DESCRIPTION OF THE PREFERRED EMBODIMENTS

With respect to the problems of the conventional solid and liquid particle aqueous suspensions, the inventors of the present invention have carefully studied the process for stably suspending solid or liquid particles in an aqueous suspension medium and, as a result, have found that when a suspension treatment is applied to a particulate solid substance or a liquid substance in an aqueous medium while skillfully utilizing at least two types of surfactants different in molecular weight from each other, the resultant composite particles in which a core composite particles are coated with a coating layer comprising the two or more different types of surfactant, can exhibit an excellent storage stability over a long period of time which is significantly longer than that which was believed to be possible in the conventional suspensions, even when the suspended particles have a large particle size of, for example, 100–1,000 μm. Also, it was found that even when a portion of the composite particles precipitates from the aqueous suspension during storage, the precipitated portion of the composite particles is easily re-suspended in the aqueous medium by a light agitation, and that the resultant aqueous suspension can be easily handled for practical use. Further, it was found that even where the particulate solid substance or the liquid substance exhibits a decreased resistance to hydrolysis when the substance is finely divided, the solid or liquid substance can be stably suspended in the form of the specific composite particles in an aqueous medium in accordance with the present invention.

The present invention was completed on the basis of the above-mentioned findings.

The particulate solid substances and the liquid substances for which the present invention is applicable must have a significantly poor solubility in the aqueous medium and thus must be substantially insoluble or scant soluble in the aqueous medium.

The aqueous suspension of composite particles of the present invention comprises (A) an aqueous suspension medium and (B) a plurality of composite particles suspended in the aqueous suspension medium.

Each composite particle comprises (a) a core consisting of a solid or liquid particle, and (b) a coating layer formed on the peripheral surface of the core particle.

In the aqueous suspension of the present invention, preferably the core particles have an average particle size of 3 to 500 μm, more preferably 10 to 100 μm and the composite particles have an average particle size of 6 to 1,000 μm, more preferably 10 to 100 μm.

The coating layer comprises (i) a high molecular weight surfactant component comprising at least one high molecular weight surfactant compound having an average molecular weight of 1100 or more, and (ii) a low molecular weight surfactant component comprising at least one low molecular weight surfactant compound which has an average molecular weight of 1100 or less and at least 400 below the average molecular weight of the high molecular weight surfactant compound.

The above-mentioned aqueous composite particle suspension can be produced in accordance with the process of the present invention, by subjecting a particulate solid substance or a liquid substance to a suspending treatment in an aqueous treating liquid comprising an aqueous suspension medium, a high molecular weight surfactant component comprising at least one high molecular weight surfactant compound having an average molecular weight of 1100 or more, and a low molecular weight surfactant component comprising at least one low molecular weight surfactant compound having an average molecular weight of 1100 or less and at least 400 below the average molecular weight of the high molecular weight surfactant compound.

The particulate solid substances and the liquid substances are preferably selected from the following groups.

(1) In organic particulate solid substances including pigments, for example, titanium dioxide, zinc oxide, lead oxide, white lead, chrome yellow, molybdenum red, ultramarine, carbon black, black iron oxide, yellow iron oxide, red iron oxide, zinc white, lithopone, chromium oxide, brass powder, aluminum powder, bronze powder, graphite, and chromium hydroxide; and particulate construction and building materials, for example, silica gel, cement, mortar, alumina cement, sands, clay minerals, and asphalt; particulate mineral materials and chemicals, for example, silver nitrate, Mercury (I) chloride, magnesium carbonate, diatomaceous earth, pearlite, bentonite, active clay, zeolite, talc, mica, sericite, kaolin, ilmenite, silicon carbide, magnesium silicate, calcium carbonate, barium carbonate, barium sulfate, silica, aluminum oxide, antimony trioxide, cerium oxide, magnesium hydrogen carbonate, activated carbon black, coal powder, anhydrous gypsum, gypsum dihydrate, and various ceramics. These inorganic substances are usable for cosmetics, deodorants, deodorizers, bath additives, liquid snow-melting agents, and ceramic premolding compositions.

(2) Organic particulate substances including waterinsoluble or scant soluble resins, pigments, dyes, medicine, cosmetic and industrial chemicals, food materials, and agricultural chemicals.

The resins usable for the present invention include, for example, polystyrene, fluorine-containing resins such as polytetrafluoroethylene, urea-formaldehyde resins, melamine-formaldehyde resins, phenol-formaldehyde resins, polyesters, polyethylene, polypropylene, polyvinyl chloride, silicone resins, and polymethyl methacrylate.

The pigments include azo pigments, diketobihydropyrol pigments, benzimiazolone pigments, phthalocyanine pigments, quinacridone pigments, isoindolinone pigments, perylene-perynone pigments, dioxazine pigments, anthraquinone pigments, dianthraquinonyl pigments, anthrapyrimidine pigments, anthanthrone pigments, indanthrone pigments, flavanthrone pigments, pyranthrone pigments, vat dye type pigments, and fluorescent brightener pigments.

The dyes include disperse dyes, natural dyes, solvent-soluble dyes, food dyes and fluorescent brightener dyes.

The above-mentioned pigments and dyes also include, for example, Pigment Red 49, Pigment Red 53, Pigment Red 3, Pigment Orange 5, Solvent Green 3, Solvent Violet 13, Pigment Yellow 1, Pigment Blue 15, Pigment Red 57, Vat Red 1, Acid Yellow 23, and Pigment Yellow 12.

The medicine, cosmetic and industrial chemicals include Mercury phenyl acetate, p-hydroxybenzoic acid, benzalkonium chloride chlorohexydine gluconate, tetracycline, cefalexin, erythromycin, chloramphenicol, aspirin, phenylbutazone, diphenhydramine hydrochloride, lidocaine, protease, macrolide antibiotics, citocaines, hormone preparation and vitamin preparation.

The food materials include wheat powder, rice powder, milk powder and starch powder.

The agricultural chemicals include pesticides, for example, insecticides, germicides and herbicides, and growth-enhancing materials, for examples fertilizers and growth hormones.

The particulate pesticides usable for the present invention include, for example, 2,4-dichlorophenoxyacetic acid (2,4-D), 2-methyl-4-chlorophenoxyacetic acid (MCP), ethyl 2-methyl-4-chlorophenoxyacetate (MCP), 2,4-dichlorophenyl-3-methoxy4-nitrophenylether (chloromethoxynyl), methyl=5-(2,4-dichlorophenyl)-2-nitrobenzoate (biphenox), 2,4,6-trichlorophenyl-4-nitrophenylether (CNP), 2-chloro-N-(4methoxy-6-methyl-1,3,5-triazine-2-il-aminocarbonyl)benzenesulfonamide, methyl=2-[3-(4-methoxy-6-methyl-1,3,5-triazine-2-yl) ureidosulfonyl]benzoate, methyl=2-[3-(4,6-dimethylpyrimidine-2-yl)ureidosulfonyl]benzoate, ethyl=2-[3-(4-chloro-6-methoxypyrimidine-2-yl)ureidosulfonyl)] benzoate, 1-(4,6-dimethoxypyrimidine-2-yl)-3-(3-ethylsulfonyl-2-pyridylsulfonyl)urea, 3-(6-methoxy-4-methyl-1,3,5-triazine-2-yl)-1-[2-(2-chloroethoxy) phenylsulfonyl]urea, methyl=2-[3-(4-methoxy-6-methyl-1,3,5-triazine-2-yl)-3-methylureidosulfonyl]benzoate, methyl=3-[3-(4-methoxy-6-methyl-1,3,5-triazine-2-yl) ureidosulfonyl]thiophene-2-carboxylate, 1-(4,6-dimethoxypyrimidine-2-yl)-3-3-(3-trifluoromethyl-2-pyridinylsulfonyl)urea, 2-(4,6-dimethoxypyrimidine-2-yl-carbamoylsulfamoyl)-N,N-dimethylnicotinamide, 3-(4,6-dimethoxy-1,3,5-triazine-2-yl)-1-[2-(2-methoxyethoxy) phenylsulfonyl]urea, 2-[3-(4,6-bis(difluoromethoxy)-pyrimidine-2-yl)ureidosulfonyl]-benzoic acid=methyl, methyl=2-[(4-ethoxy-6-methylamino-1,3,5-triazine-2-yl) carbamoylsulfamoyl]benzoate, methyl=2-[3-(4,6-dimethoxypyrimidine-2-yl)ureidosulfonylmethyl]benzoate (Bensulfronmethyl), ethyl=5-[3-(4,6-dimethoxypyrimidine-2-yl)ureidosulfonyl]-1-methylpirazole-4-carboxylate (Pyrazosulfron), N-[2-chloroimidazole(1,2-a)pyridine-3-yl-sulfonyl]-N'-(4,6-dimethoxy-2-pyrimidyl)urea (Imazosulfron), 2,4-bis(ethylamino)-6-methylthio-1,3,5-triazine (Simetrin), 2,4-bis(isopropylamino)-6-methylthio-1,3,5-triazine (Prometrin), 2-(1,2-dimethylpropylamino)-4-ethylamino-6-methylthio-1,3,5-triazine (Dimetametrin), 4-(2,4-dichlorobenzoyl)-1,3-dimethyl-1H-pyrazole-5-yl-p-toluenesulfonate (Pyrazolate), 4-(2,4-dichlorobenzoyl)-1,3-dimethyl-5-phenacyloxy-1H-pyrazole (Pyrazoxyphen), 4-(2,4-dichloro-3-methylbenzoyl)-1,3-dimethyl-5-(4-methylphenacyloxy)-1H-pyrazole (Benzophenap), 5-tert-butyl-3-(2,4-dichloro-5-isopropoxyphenyl)-1,3,4-oxadiazole-2(3H)-one (Oxadiazon), 2-(2,4-dichloro-3-methylphenoxy)-propionanilide (Chlomeplop), 2-(2-naphthyloxy)propionanilide (Naploanilide), 3',4'-dichloropropionanilide (Propanyl), 3-isopropyl-1H-2,1,3-benzothiadiazine-4-(3H)one-2,2-dioxide (Pentazon), 3-(3,4-dichlorophenyl)-1,1-dimethylurea (Diuron), 2',3'-dichloroethoxymethoxybenzanilide (HW-52), and 3,5-xylyl=N-methylcarbamate (XMC).

The above-mentioned inorganic and organic particulate substances may be in the form of spheres, fibers, rods, plates, sands or flakes.

(3) Liquid substances including liquid monomers, oligomers, polymers, liquid vehicles for paints, liquid food substances, liquid medicines, liquid cosmetic materials, liquid perfumes, toiletry chemicals and liquid agricultural chemicals.

The liquid monomers, oligomers and polymers include, for example, polybutadiene, polyvinyl chloride resins, polyvinyl acetate resins, acrylic resins, epoxy resins, polyester resins, and polyether resins.

The liquid paint vehicles includes, for example, boiled oil, varnish, enamel, cellulose lacquers, alkyd resins and aminoalkyd resins.

The liquid food substances includes, for example, edible vegetable and animal oils.

The liquid medicines include, for example, methyl salicylate, clofibrate, diphenhydramine, and dimercaprol.

The liquid cosmetic materials include, for example, olive oil, organic fatty acids such as oleic acid, vaseline, and benzyl benzoate.

The liquid agricultural chemicals (pesticides) include, for example, ethyl-4-[4-(4-trifluoromethylphenoxy)phenoxy]-2-pentenoate, butyl-2-[4(5-trichloromethyl-2-pyridyloxy) phenoxy]-propionate, N-benzyl-N-isopropylpivalamide, N,N-diallyl-2chloroacetamide, S-ethyl-N,N-diethylcarbamate, 4-octanoyloxy-3,5-dibromobenzonitrile, 2-(2-chlorobenzylthio)-5-propyl-1,3,4-oxadiazole, 2-(1,2-dimethylpropylamino)-4-ethylamino-6-methylthio-1,3,5-triazine, hexachloroacetone, tris[2-(2,4-dichlorophenoxy) ethyl]phosphite, and 2-(2-chlorophenyl)methyl-4,4-dimethyl-3-isooxazolidinone.

The particulate solid substance and the liquid substances can be used alone ore in a mixture of two or more thereof. When used in the mixture, they can be in any mixing ratio. The particulate solid substance is not limited one having a specific particle size. Preferably, the particulate solid substance has a particle size of 1000 μm or less, for example, 3 to 500 μm. When the process of the present invention is applied a liquid substance, the liquid substance is divided into liquid particles having a desired particle size, for example, 0.5 to 300 μm by the suspending treatment.

In the aqueous suspension and the process for producing the same of the present invention, the content of the particulate solid substance or the liquid substance is not limited to a specific range of values. However, in consideration of handling ease and cost, the content of the particulate solid substance or the liquid substance in the aqueous suspension is preferably 0.1 to 75% by weight based on the total weight of the target aqueous suspension.

The high molecular weight surfactant compounds usable for the present invention are not limited to a specific type of compounds as long as the compounds have an average molecular weight of 1100 or more and 400 or more above the average molecular weight of the low molecular weight surfactant compounds and are usable for the process of the present invention to stably suspending (dispersing or emulsifying) the particulate solid substance or the liquid substance.

Preferably, the high molecular weight surfactant compounds are selected from those mentioned below. These compound preferably have an average molecular weight of 1800 or more, more preferably 2,000 to 1,000,000, still more preferably 3,000 to 700,000.

Also, the high molecular weight surfactant compounds usable for the present invention preferably have two or more ionic (anionic or cationic) groups per molecule thereof.

Examples of the high molecular weight surfactant compounds (1) Alkali metal salts, amine salts and ammonium salts of acrylic acid polymers.
(2) Copolymers of maleic anhydride with acrylic acid and alkali metal salts, amine salts and ammonium salts of the copolymers.
(3) Copolymers of itaconic acid with acrylic acid and alkali metal salts, amine salts and ammonium salts of the copolymers.
(4) Block copolymers of polyoxypropylenes (which will be referred to as "POP" hereinafter) with polyoxyethylenes (which will be referred to as "POE" hereinafter).
(5) Copolymers of cationic monomers with nonionic monomers (for example, copolymers of alkyl vinylpylidinums with aducts of alkyl vinyl alcohols with alkyleneoxides.
(6) Alkali metal salts of polystyrenesulfonic acids.
(7) Melamine sulfonic acid-formaldehyde polycondensation products.
(8) Alkali metal salts of sulfonated styrenemaleic anhydride copolymers.
(9) Sodium salts of polyepoxysuccinic acid.
(10) Polycondensation products of sodium naphthalenesulfonate with formaldehyde.
(11) Polyvinyl alcohol.
(12) Dextrin-fatty acid esters.
(13) Carboxymethylcellulose.
(14) Ethylenediamine-POP.POE block polymers.
(15) Copolymers of alkylaminoalkyl(meth) acrylamides with (meth)acrylic acid alkylacrylamides or acrylonitrile.
(16) Graft copolymerization products of cationic derivatives of linear polysaccharides with olefin monomers.
(17) Poly-4-vinylpyridine-type cationic surfactants.

The high molecular weight surfactant compounds may be employed alone or preferably in a mixture of two or more having the same type of ionic property as each other or of one or more anionic or cationic compounds with one or more nonionic compounds, to provide the high molecular weight surfactant component. Among the above-mentioned high molecular weight surfactant compounds, the block copolymers (4) having the POP segments with a polymerization degree of 2 to 200 and the POE segments with a polymerization degree of 2 to 400 are preferably employed for the present invention.

In the present invention, the low molecular weight surfactant component comprises at least one low molecular weight surfactant compound having an average molecular weight of 1100 or less and of 400 below the molecular weight of the high molecular weight surfactant compound. Also, preferably, the ionic property of the low molecular weight surfactant compound does not badly affect on the ionic property of the high molecular weight surfactant compound. Generally, the average molecular weight of the low molecular weight surfactant compounds is preferably in the range of from 100 to 1100, more preferably 300 to 1100.

For example, where the high molecular weight surfactant component contains an anionic high molecular weight surfactant compound, preferably the low molecular weight surfactant component comprises at least one anionic low molecular weight surfactant compound, or at least one nonionic low molecular weight surfactant compound, or a mixture of at least one anionic low molecular weight surfactant compound with at least one nonionic low molecular weight surfactant component.

Also, where the high molecular weight surfactant component contains a cationic high molecular weight surfactant compound, preferably the low molecular weight surfactant component comprises at least one cationic low molecular weight surfactant compound, or at least one nonionic low molecular weight surfactant compound, or a mixture of at least one cationic low molecular weight surfactant compound with at least one nonionic low molecular weight surfactant component.

As long as the above-mentioned conditions are attained, the low molecular weight surfactant component may comprises two or more low molecular weight surfactant compounds.

The anionic low molecular weight surfactant compounds usable for the present invention are not limited to specific type of compounds. Preferably, the anionic low molecular weight surfactant compounds are selected from alkyl sulfuric acid salts, organic sulfonic acids and salts thereof, polyether sulfuric acid salts, sulfosuccinic acid salts, and organic phosphoric acid compounds and salts thereof.

The alkylsulfuric acid salts include sodium laurylsulfate, triethanolamine laurylsulfate, ammonium laurylsulfate and potassium laurylsulfate.

The organic sulfonic acids and salts thereof include lignin sulfonic acid and alkylarylsulfonic acids, for example, alkylbenzenesulfonic acids and alkylnaphthalenesulfonic acids, and salts of the above-mentioned sulfonic acids.

The polyethersulfuric acid salts include polyoxyethylenealkylethersulfuric acid salts, and polyoxyethylenealkylarylethersulfuric acid salts.

The sulfosuccinic acid salts include lauryl disodium sulfosuccinate, lauryl disodium polyoxyethylenealkylsulfosuccinate and dioctyl sodium sulfosuccinate.

The organic phosphoric acid compounds and salts thereof include polyoxyethylenealkylarylether-phosphoric acids, polyoxyethylenephenylether-phosphoric acids and salts thereof.

The cationic low molecular weight surfactant compounds usable for the present invention are preferably selected from alkyltrimethylammonium halides, alkyldimethylbenzylammonium halides, stearylpentaethoxyammonium chloride, and chloro-o-[2-hydroxy-3-(trimethylammonio)propyl] hydroxyethyl cellulose.

The alkyltrimethylammonium chlorides include lauryltrimethylammonium chloride, cetyltrimethylammonium chloride, stearyltrimethylammonium chloride, lauryltrimethylammonium bromide, and stearyltrimethylammonium bromide.

The alkyldimethylbenzylammonium halides include lauryldimethylbenzylammonium chloride, stearyldimethylbenzylammonium chloride, and tri(polyoxyethylene) stearylammonium chloride.

The nonionic low molecular weight surfactant compounds usable for the present invention may be selected from alkylolamides, polyoxyethylenealkylphenylethers, polyoxyethylenealkylethers, polyethyleneglycol-fatty acid esters, sorbitan-fatty acid esters, sorbitol-fatty acid esters, polyoxyethylenepolyoxypropylenealkyl ethers, polyoxyethylenealkylarylethers, polyoxyethylenestyrylphenylethers, polyoxyethylenealkylesters, and polyoxyethylenestyrylphenylether polymers.

The alkylolamides include lauric acid-diethanolamide, lauric acid-myristic acid-diethanolamide, myristic acid-diethanol amide and polyoxyethylene-stearic acid amide.

The polyoxyethylenealkylphenylethers include polyoxyethyleneoctylphenylether, polyoxyethylenenonylphenylether, and polyoxyethylenedinonylphenylether.

The polyoxyethylenealkylethers include polyoxyethylenelaurylether, polyoxyethylenetridecylether, polyoxyethyleneoleylether, polyoxyethylenecetylether, and polyoxyethylenestearylether.

The polyethyleneglycol-fatty acid esters include polyethyleneglycol monooleate, polyethyleneglycol dioleate, polyethyleneglycol monostearate, ethyleneglycol distearate, and polyethyleneglycol distearate.

The sorbitan-fatty acid esters include decaglycerol monocaprylate, glycerol monostearate, sorbitan monocaprylate, sorbitan monolaurate, sorbitan monopalmitate, sorbitan monostearate, sorbitan distearate, sorbitan trioleate, sorbitan sesquioleate, polyoxyethylenesorbitan monolaurate, polyoxyethylenesorbitan monopalmitate, polyoxyethylenesorbitan monostearate, and polyoxyethylenesorbitan trioleate.

The sorbitol-fatty acid esters include polyoxyethylenesorbitol monooleate and polyoxyethylenesorbitol tetraoleate. The polyoxyethylenepolyoxypropylenealkylethers include polyoxyethylenepolyoxypropylene alkylether-blocked polyoxyethylenepolyoxypropyleneglycol, and ethylenediaminetetrapolyoxyethylenepolyoxypropylene.

Among the above-mentioned low molecular weight surfactant compounds, the preferred compounds are POE (polymerization degree=9 to 25) styrylphenylethers, POE (polymerization degree=2 to 15) alkylarylethers, and POE (polymerization degree=2 to 10) alkylethers.

These compounds may be employed alone or in a mixture of two or more thereof or in a mixture of one or more thereof with one or more other low molecular weight surfactant compounds.

Most preferably, the POE (polymerization degree=9 to 25) styrylphenylethers, the POE (polymerization degree=2 to 15) alkylarylethers and POE (polymerization degree=2 to 10) alkylethers are employed alone or in a mixture of two or more thereof.

In the present invention, it is preferable that the high molecular weight surfactant component has an average molecular weight of 1800 to 1,000,000, more preferably 3,000 to 700,000, and the low molecular weight surfactant component has an average molecular weight of 100 to 1100, more preferably 300 to 1,100.

In the present invention, the aqueous suspension medium may optionally further comprise a suspension stabilizer.

Particularly, where the high molecular weight surfactant compound in the high molecular weight surfactant component is nonionic, or has only one ionic group per molecule of the compound, the suspension medium preferably contains the suspension stabilizer. The suspension stabilizer comprises at least one member selected from inorganic and organic water-soluble salts. These inorganic and organic water-soluble salts may be selected from, for example, water-soluble salts of alkali metals, alkaline earth metals and ammonia with sulfuric acid, nitric acid, phosphoric acid, hydrochloric acid and acetic acid. These salts may be employed alone or in a mixture of two or more thereof.

Preferred inorganic and organic salts are, for example, magnesium sulfate, calcium sulfate, potassium sulfate, sodium sulfate, ammonium sulfate, magnesium nitrate, calcium nitrate, potassium nitrate, sodium nitrate, ammonium nitrate, magnesium phosphate, calcium phosphate, potassium phosphate, sodium phosphate, ammonium phosphate, magnesium chloride, calcium chloride, potassium chloride, sodium chloride, ammonium chloride, magnesium acetate, calcium acetate, potassium acetate, sodium acetate and ammonium acetate. A particularly preferred salt is magnesium sulfate.

In the present invention, where the high molecular weight surfactant compound has two or more ionic groups per molecule thereof, the suspension stabilizer may be omitted.

In the present invention, the core solid or liquid particle, the high molecular weight surfactant component, the low molecular weight surfactant component and optionally the suspension stabilizer form together a composite particle.

Namely, the coating layer formed on the core particle has a two-layered structure consisting of an inner coating layer formed on the peripheral surface of the core particle and comprising the high molecular weight surfactant component and an outer coating layer formed on the inner coating layer and comprising the low molecular weight surfactant component.

The outer coating layer optionally contains the suspension stabilizer. The suspension stabilizer is mainly distributed in an interface between the inner coating layer and the outer coating layer so as to enhance the bonding between the inner layer and the outer layer.

The average particle size of the composite particles of the present invention is variable responding to the average particle size of the core solid or liquid particles, and is usually 1000 μm or less, more preferably 6 to 550 μm.

Where the composite particles are suspended in the aqueous suspension medium, even when the composite particles have a large particle size of, for example, 100 to 1000 μm, the resultant aqueous suspension exhibits a significantly excellent stability during storage, and even if a portion of the composite particles is precipitated, the precipitated portion of the composite particles can be easily re-suspended by a light agitation.

With respect to the mechanism of the high suspension stability of the composite particles of the present invention, it is believed that the higher molecular weight surface component is absorbed on the peripheral surfaces of the suspended core particles to form an inner coating layer, and the interfaces between the aqueous suspension medium and the inner coating layer surfaces are significantly stabilized by the outer layers comprising the high molecular weight surfactant component and optionally the suspension stabilizer formed on the inner coating layer. The specific two layered coating layers effectively prevent the secondary aggregation and precipitation of the composite particles in the aqueous suspension medium over a long period of time.

Also, the specific two-layered coating layers causes the aggregated and precipitated composite particles to be easily separated from each other and re-suspended with a high stability, by a light agitation.

Of course, in the aqueous medium in the aqueous suspension of the present invention, portions of the high and low molecular weight surfactant components and optionally the suspension stabilizer which are not adhered to the core particles, are present.

In the present invention, the aqueous suspension medium optionally contains an additive comprising at least one member selected from, for example, dispersing aids viscosity-regulating agents, preservatives, mildewproofing agents, antifreezing agents, defoaming agents, chemical stabilizers and shaping agents.

The dispersion aids include magnesium stearate.

The viscosity-regulating agents include, for example, xanthane gum, gua gum, gum tragacanth, gum arabic, casein, dextrin, carboxymethyl cellulose, carboxymethyl starch-sodium salt, sodium alginate, hydroxyethyl cellulose, carboxyethyl cellulose, methyl cellulose, hydroxypropyl cellulose, hydroxyethyl cellulose, polyvinyl alcohol, polyacrylic acid and derivatives thereof, colloidal magnesium silicate hydrate, and colloidal aluminum magnesium silicate. These compounds can be used alone or in a mixture of two or more thereof.

The preservatives and mildewproofing agents include, for example, p-chloro-m-xylenol, p-chloro-m-cresol, butyl p-hydroxybenzoate, sorbitan fatty acid, and potassium sorbate. They can be employed alone or in a mixture of two or more thereof.

The antifreezing agents include, for example, ethyleneglycol, diethyleneglycol, propyleneglycol, glycerol, ethyleneglycolmonomethylether, diethyleneglycol monomethyl ether, and methanol. They can be used alone or in a mixture of two or more thereof.

The defoaming agents usable for the present invention can be selected from conventional silicone, fatty acid and mineral oil type defoaming agents.

The chemical stabilizers for the suspended core particles include antioxidants and ultraviolet ray-absorbing agents.

The solid particles optionally contain a shaping agent which can be selected from the conventional shaping agent, for example, Aerosil 200 (trademark, made by Nihon Aerosil K. K.).

In the aqueous suspension of the present invention, the core particles are preferably present in an amount of 0.1 to 75%, more preferably 0.1 to 50%, by weight based on the total weight of the aqueous suspension.

In the aqueous suspension of the present invention, the high molecular weight surfactant component is preferably present in an amount of 0.1 to 5%; more preferably 0.5 to 3%, by weight, and the low molecular weight surfactant component is preferably present in an amount of 0.1 to 25% by weight, more preferably 0.5 to 10% by weight, each based on the total weight of the aqueous suspension. Also, where the suspension stabilizer is used, the content of the suspension stabilizer in the aqueous suspension is preferably 0.1 to 30%, more preferably 0.5 to 10%, by weight based on the total weight of the aqueous suspension.

In an embodiment of the process of the present invention, the suspending treatment includes: (a) a first suspending treatment in which the particulate solid substance or the liquid substance is firstly suspended in a first aqueous treating liquid containing the high molecular weight surfactant component to provide a first aqueous suspension, and (b) a second suspending treatment in which the low molecular weight surfactant component is admixed into the first aqueous suspension, and in the resultant admixture, the first suspended particles are secondly suspended to provide a second aqueous suspension, thereby to provide the coating layer having an inner coating layer formed on the peripheral surface of the core solid particle and comprising the high molecular weight surfactant component and an outer coating layer formed on the inner coating layer and comprising the low molecular weight surfactant component.

In the above-mentioned embodiment of the process of the present invention, at a stage of during or before the first suspending treatment, or between the first and second suspending treatments, or during or after the second suspending treatment, a suspension-stabilizer comprising at least one member selected from inorganic and organic water-soluble salts is optionally mixed into the aqueous treating liquid, thereby to cause the suspension stabilizer to be distributed in the interface between the inner coating layer and the outer coating layer of each composite particle.

In another embodiment of the process of the present invention, the particulate solid substance or the liquid substance is mixed into the first aqueous treating liquid containing the high molecular weight surfactant component, the resultant mixture is subjected to the first suspending treatment, the resultant first suspension is mixed with the aqueous suspension stabilizer, the resultant mixture is subjected to an intermediate suspending treatment; the resultant intermediate suspension is mixed with the low molecular weight surfactant component, and the resultant mixture is subjected to the second suspending treatment, to provide an aqueous suspension of the composite particles.

In still another embodiment of the process of the present invention, the particulate solid substance or the liquid substance is subjected to a pre-suspending treatment in an aqueous treating liquid containing the suspension stabilizer; the resultant aqueous presuspension is mixed with the high molecular weight surfactant component; the resultant mixture is subjected to the first suspending treatment; the resultant first aqueous suspension is mixed with the low molecular weight surfactant component; and the resultant mixture is subjected to the second suspending treatment, to provide an aqueous suspension of the composite particles.

In a further embodiment of the process of the present invention, the particulate solid substance or the liquid substance is subjected to the first suspending treatment in the aqueous treating liquid comprising the high molecular weight surfactant component; the resultant first aqueous suspension is mixed with the low molecular weight surfactant component; the resultant mixture is subjected to the second suspending treatment; and the resultant second aqueous suspension is mixed with the suspension stabilizer, to provide an aqueous suspension of the composite particles.

In the above-mentioned process of the present invention, each suspending treatment is carried out by agitating the aqueous treating liquid containing the particulate solid substance or the liquid substance with an agitator at a revolution rate of 3000 to 15000 rpm at a temperature lower than the boiling temperature of the aqueous treating liquid, preferably 20° to 80° C., more preferably 20° to 40° C.

In each suspension treatment, the particle size of the core solid or liquid particles, the amount and composition of the coating layers and the particle size of the resultant composite particles can be adjusted to the desired values by using a suitable type of agitator having agitating wings with an appropriate form and dimensions, and controlling the agitating rate and time and the temperature of the aqueous treating liquid. There is no limitation to the type of the agitator. For example, homomixer, homogenizer, Dynomill, and air mill can be used for the process of the present invention.

The particle size of the composite particles suspending in the aqueous suspension of the present invention can be easily determined by a particle size tester. For example, a laser type particle size tester available under the trademark of Coaltar LS130, from K. K. Nikkakisha can be used.

The preparation of the aqueous suspension in accordance with the process of the present invention can be effected by usual aqueous suspension-preparation procedures without using specific procedure or apparatus.

The process of the present invention can be carried out, for example, in the following manner.

First, a high molecular weight surfactant component is mixed with an aqueous dispersion of particulate solid substance or with a liquid substance in an amount of 0.1 to 75% by weight based on the total weight of the target aqueous suspension, the resultant mixture is agitated by an agitator, for example, a homomixer at a rotation rate of 3,000 to 15,000 rpm for 3 to 20 minutes while maintaining the temperature of the mixture at a level lower than the boiling temperature of the mixture, for example, 20° to 80° C., to apply a first suspension treatment to the particulate solid substance or to the liquid substance. To the resultant first aqueous suspension is added 0.1 to 100% by weight, preferably 0.1 to 10% by weight, of a suspension-stabilizer consisting of at least one member selected from inorganic salts, for example, magnesium sulfate, calcium sulfate, potassium sulfate, sodium sulfate, magnesium chloride, calcium chloride, potassium chloride, sodium chloride, magnesium nitrate, calcium nitrate, potassium nitrate, and sodium nitrate, and organic salts, for example, potassium acetate, sodium acetate and ammonium acetate. In this stage, optionally, at least one additive selected from, for example, defoaming agents, viscosity-regulating agents, preservatives, mildewproofing agents, antifreezing agents, and chemical stabilizers for the core particles is added to the first aqueous suspension. The suspension stabilizer can be easily added by previously dissolving it in water to provide an aqueous solution thereof. However, the suspension stabilizer may be added in the state of a solid to the first aqueous suspension. After the addition of the suspension stabilizer, the resultant admixture is agitated by an agitator, for example, a homomixer, at a rotation rate of 3,000 to 15,000 rpm at a temperature, for example, 20° to 80° C. for 3 to 20 minutes to provide an intermediate aqueous suspension.

To the resultant suspension is added the low molecular weight surfactant component and the resultant admixture is subjected to a second suspending treatment by agitating it by an agitator, for example, a homomixer, at a rotation rate of 3,000 to 15,000 rpm at a temperature, for example, 20° to 80° C., for 3 to 20 minutes.

A target aqueous suspension of composite particles are obtained.

Alternatively, the composite particle aqueous suspension of the present invention can be produced by the following procedures.

To an aqueous dispersion of a particulate solid substance or a liquid substance in an amount of 0.1 to 75% by weight based on the total weight of the target aqueous suspension, a suspension stabilizer is mixed in an amount 0.1 to 100% by weight, preferably 0.1 to 10% by weight based on the weight of the particulate solid substance or the liquid substance. In this stage, optionally, an additive, for example, a defoaming agent is added together with the suspension stabilizer.

The suspension stabilizer may be in the state of an aqueous solution or in solid state. Then, the resultant mixture is subjected to a pre-suspending treatment using an agitator, for example, homomixer at a rotation rate of 3,000 to 15,000 rpm at room temperature for 3 to 20 minutes. To the resultant aqueous pre-suspension, a high molecular weight surfactant component is mixed and the resultant mixture is subjected to a first suspending treatment by agitating the mixture with an agitator, for example, a homomixer at a rotation rate of 3,000 to 15,000 rpm at room temperature for 3 to 20 minutes.

The resultant first aqueous suspension was mixed with a low molecular weight surfactant component, and the resultant mixture is subjected to a second suspending treatment by using an agitator, for example, a homomixer, at a rotation rate of 3,000 to 15,000 rpm at room temperature for 3 to 20 minutes. A target aqueous suspension of the composite particles is obtained. Otherwise, the aqueous suspension of the composite particles of the present invention can be prepared by the following procedures.

First, a high molecular weight surfactant component is mixed with an aqueous dispersion of a particulate solid substance or with a liquid substance in an amount of 0.1 to 75% by weight based on the total weight of the target aqueous suspension. The mixture is subjected to a first suspending treatment using an agitator, for example, a homomixer at a rotation rate of 3,000 to 15,000 rpm at room temperature for 3 to 20 minutes. To the resultant first aqueous suspension, a low molecular weight surfactant component is mixed, and the resultant mixture is subjected to a second suspending treatment using an agitator, for example, a homomixer at a rotation rate of 3,000 to 15,000 rpm at room temperature for 3 to 20 minutes. To the resultant second aqueous suspension, a suspension stabilizer is added in an amount of 0.1 to 100% by weight, preferably 0.1 to 10% by weight, based on the weight of the particulate solid substance or the liquid substance. In this stage, an additive, for example, a defoaming agent, may be added to the second aqueous suspension, if necessary. The suspension stabilizer may be employed in the state of an aqueous solution or in the solid state. The resultant mixture is optionally subjected to a post-suspending treatment using an agitator, for example, a homomixer at a rotation rate of 3,000 to 15,000 rpm at room temperature for 3 to 20 minutes. A target aqueous suspension of the composite particles can be obtained.

In the process of the present invention, the total amount of the high and low molecular weight surfactant components is variable depending on the amount of the particulate solid substance or the liquid substance, and preferably is in the range of 0.2 to 100% by weight, more preferably 0.5 to 10% by weight, based on the weight of the particulate solid substance or the liquid substance. Also, the amount of the high molecular weight surfactant component is preferably 0.1 to 10% by weight, based on the particulate solid substance or the liquid substance.

For the purpose of enhancing the suspending property of the particulate solid substance or the liquid substance in the aqueous medium, optionally, before the particulate solid substance or the liquid substance is mixed into the aqueous medium, a portion of the low molecular weight surfactant component in an amount corresponding to 50% by weight or less of the total weight of the low molecular weight surfactant component is added into the aqueous medium.

EXAMPLE

The composite particle aqueous suspension and the process for producing the same of the present invention will be further explained by the following examples which are merely representative and do not limit the scope of the present invention in any way.

Example 1

One part by weight of a high molecular weight surfactant component consisting of a POE (polymerization degree=5)-POP (polymerization degree=30) block copolymer having a molecular weight of 2917, 1 part by weight of POE (polymerization degree=14)-styrylphenylether having a molecular weight of 1015, 15 parts by weight of 3',4'-dichloropropionanilid (pesticide) having a average particle size of 50 μm and 15 parts by weight of 3-(3,4-dichlorophenyl)-1,1-dimethylurea (pesticide) having an average size of 50 μm were mixed into 58.2 parts by weight of water.

The resultant mixture was subjected to a first suspending treatment in which the mixture was agitated by a homomixer at a rotation rate of 10,000 rpm at a temperature of 40° C. or less for 30 minutes.

Into the resultant first aqueous suspension, 0.4 part by weight of magnesium stearate, 1 part by weight of magnesium sulfate, 4 parts by weight of ethylene glycol and 0.4 part by weight of a shaping agent (trademark: Aerosil 200, made by Nihon Aerosil K. K.) were mixed.

The resultant mixture was subjected to an intermediate suspending treatment in which the mixture was agitated by a homomixer at a rotation rate of 10,000 rpm at a temperature of 40° C. or less for 30 minutes.

The resultant intermediate aqueous suspension was mixed with 3 parts by weight of a low molecular weight surfactant component consisting of 0.8 part of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652, and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 rpm at a temperature of 40° C. or less for 5 minutes.

A uniform aqueous suspension of composite particles including the pesticide and having an average particle size of 20 μm was obtained.

The aqueous suspension in an amount of 100 ml was placed in a precipitation cylinder having a capacity of 120 m and left to stand at a temperature of 50° C. for one month, and a degree of precipitation of the composite particles was measured. The degree of precipitation was determined from the equation (1)

$$PD(\%)=H_1/H_0 \times 100 \qquad (1)$$

wherein PD represents a degree of precipitation of the composite particles, $H_1$ represents a height of a stratum consisting of the precipitate formed in the precipitation cylinder and $H_0$ represents a height of the aqueous suspension in the precipitation cylinder. As a result, the degree of precipitation was 1%. The precipitate was fully re-suspended by turning the cylinder upside down three times or less.

Example 2

One part by weight of a high molecular weight surfactant component consisting of a POE (polymerization degree=5)-POP (polymerization degree=30) block copolymer having a molecular weight of 2917, 1 part by weight of POE (polymerization degree=14)-styrylphenylether having a molecular weight of 1015, and 30 parts by weight of a white pigment consisting of particulate titanium dioxide having a particle size of 0.5 to 2.5 μm were mixed into 58.2 parts by weight of water.

The resultant mixture was subjected to a first suspending treatment in which the mixture was agitated by a homomixer at a rotation rate of 10,000 rpm at a temperature of 40° C. or less for 30 minutes.

Into the resultant first aqueous suspension, 1 part of Pronal EX300 (trademark, an anti-foaming agent, made by Toho Kagakukogyo K. K.), 0.4 part by weight of magnesium stearate, 1 part by weight of magnesium sulfate, 4 parts by weight of ethylene glycol and 0.4 part by weight of a shaping agent (trademark: Aerosil 200, made by Nihon Aerosil K. K.) were mixed.

The resultant mixture was subjected to an intermediate suspending treatment in which the mixture was agitated by a homomixer at a rotation rate of 10,000 rpm at a temperature of 40° C. or less for 30 minutes.

The resultant intermediate aqueous suspension was mixed with 3 parts by weight of a low molecular weight surfactant component consisting of 0.8 part of a POE (polymerization degree 6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652, and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 rpm at a temperature of 40° C. or less for 5 minutes.

A uniform aqueous suspension of composite particles including the white pigment and having a particle size of 0.6 to 5 μm was obtained.

The same precipitation test as that in Example 1 was carried out at a temperature of 50° C. for one week. As a result, the degree of precipitation was 1%. The precipitate was completely re-suspended by turning the cylinder upside down three times or less.

Example 3

One part by weight of a high molecular weight surfactant component consisting of a POE (polymerization degree=5)-POP (polymerization degree=30) block copolymer having a molecular weight of 2917, 1 part by weight of POE (polymerization degree=14)-styrylphenylether having a molecular weight of 1015, and 30 parts by weight of liquid methyl salicylate were mixed into 58.2 parts by weight of water.

The resultant mixture was subjected to a first suspending treatment in which the mixture was agitated by a homomixer at a rotation rate of 10,000 rpm at a temperature of 40° C. or less for 30 minutes to suspend the methyl salicylate in the form of particles having an average particle size of 30 μm.

Into the resultant first aqueous suspension, 0.4 part by weight of magnesium stearate, 1 part by weight of magnesium sulfate, 4 parts by weight of ethylene glycol and 0.4 part by weight of Carplex were mixed.

The resultant mixture was subjected to an intermediate suspending treatment in which the mixture was agitated by a homomixer at a rotation rate of 10,000 rpm at a temperature of 40° C. or less for 30 minutes.

The resultant intermediate aqueous suspension was mixed with 3 parts by weight of a low molecular weight surfactant component consisting of 0.8 part of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652, and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 rpm at a temperature of 40° C. or less for 5 minutes.

A uniform aqueous suspension of composite particles including the liquid methyl salicylate core particles and having an average particle size of 25 μm was obtained.

The same precipitation test as in Example 1 was carried out at a temperature of 50° C. for one month. As a result, the degree of precipitation was 5% or less. The precipitate was completely re-suspended by turning the cylinder upside down three times or less.

Example 4

One part by weight of a high molecular weight surfactant component consisting of a POE (polymerization degree=5)-POP (polymerization degree=30) block copolymer having a molecular weight of 2917, 1 part by weight of POE (polymerization degree=14)-styrylphenylether having a molecular weight of 1015, and 30 parts by weight of a silica gel having an average particle size of 3 μm.

The resultant mixture was subjected to a first suspending treatment in which the mixture was agitated by a homomixer at a rotation rate of 10,000 rpm at a temperature of 40° C. or less for 19 minutes.

Into the resultant first aqueous suspension, 0.4 part by weight of magnesium stearate, 1 part by weight of sodium sulfate, and 4 parts by weight of ethylene glycol.

The resultant mixture was subjected to an intermediate suspending treatment in which the mixture was agitated by a homomixer at a rotation rate of 10,000 rpm at a temperature of 40° C. or less for 19 minutes.

The resultant intermediate aqueous suspension was mixed with 3 parts by weight of a low molecular weight surfactant component consisting of 0.8 part of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652, and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 rpm at a temperature of 40° C. or less for 5 minutes.

A uniform aqueous suspension of composite particles including the silica particles and having an average particle size of 15 μm was obtained.

The same precipitation test as in Example 1 was applied to the resultant suspension at a temperature of 50° C. for one week. As a result, the degree of precipitation was 1%. The precipitate was completely re-suspended by turning the cylinder upside down three times or less.

Example 5

A particulate pesticide consisting of 3',4'-dichloropropionanilide having an average particle size of 50 μm in an amount of 30 parts by weight, 0.4 part by weight of magnesium stearate, 1 part by weight of magnesium chloride and 4 parts by weight of ethylene glycol were mixed into 58.2 parts by weight.

The resultant mixture was subjected to a pre-suspending treatment in which the mixture was agitated by a homomixer at a rotation rate of 10,000 rpm at a temperature of 40° C. or less for 15 minutes.

Into the resultant aqueous pre-suspension, 1 part by weight of a high molecular weight surfactant component consisting of sodium polyacrylate having a molecular weight of 300,000 and 1 part of POE (polymerization degree of 14) styrylphenylether were mixed.

The resultant mixture was subjected to a first suspending treatment in which the mixture was agitated by a homomixer at a rotation rate of 10,000 rpm at a temperature of 40° C. or less for 15 minutes.

The resultant first aqueous suspension was mixed with 3 parts by weight of a low molecular weight surfactant component consisting of 0.8 part of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652, and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 rpm at a temperature of 40° C. or less for 5 minutes.

A uniform aqueous suspension of composite particles including the pesticide and having an average particle size of 30 μm was obtained.

The same precipitation test as in Example 1 was applied to the composite particle aqueous suspension at a temperature of 50° C. for one month. As a result, the degree of precipitation was 1%. The precipitate was completely re-suspended by turning the cylinder upside down three times or less.

Example 6

One part by weight of a high molecular weight surfactant component consisting of a cationic high molecular weight surfactant compound having a molecular weight of 40,000, 1 part by weight of POE (polymerization degree=14)-styrylphenylether having a molecular weight of 1015, and 30 parts by weight of a pesticide consisting of particulate 3-(3,4-dichlorophenyl)-1,1-dimethylurea having an average particle size of 55 μm.

The resultant mixture was subjected to a first suspending treatment in which the mixture was agitated by a homomixer at a rotation rate of 10,000 rpm at a temperature of 40° C. or less for 10 minutes.

The resultant first aqueous suspension was mixed with 3 parts by weight of a low molecular weight surfactant component consisting of 0.8 part of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652, and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 rpm at a temperature of 40° C. or less for 5 minutes.

Then the resultant second aqueous suspension was mixed with 0.4 part by weight of magnesium stearate, 1 part by weight of calcium chloride, and 4 parts by weight of ethylene glycol.

The resultant mixture was subjected to a post-suspending treatment in which the mixture was agitated by a homomixer at a rotation rate of 10,000 rpm at a temperature of 40° C. or less for 10 minutes.

A uniform aqueous suspension of composite particles including the pesticide and having an average particle size of 35 μm was obtained.

The aqueous suspension was subjected to the same precipitation test as in Example 1, at a temperature of 50° C. for one month. As a result, the degree of precipitation was 1%. The precipitate was fully re-suspended by turning the cylinder upside down three times or less.

Example 7

One part by weight of a high molecular weight surfactant component consisting of a POE (polymerization degree=5)-POP (polymerization degree=30) block copolymer having an average molecular weight of 2917, 1 part by weight of POE (polymerization degree=14) styrylphenylether having a molecular weight of 1015, and 30 parts by weight of a ground calcium carbonate pigment (trademark: Tankaru Super 1500, made by Maruo Calcium K. K.) having a particle size of 0.5 to 5.0 μm were mixed into 58.2 parts by weight of water.

The resultant mixture was subjected to a first suspending treatment by agitating the mixture by a homomixer at a rotation rate of 10,000 at a temperature of 40° C. or less for 30 minutes.

Into the resultant first aqueous suspension, 1 part by weight of Pronal EX300, 0.4 part by weight of magnesium stearate, 1 part by weight of magnesium sulfate, 4 parts by weight of ethyleneglycol and 0.4 part by weight of Carplex were mixed.

The resultant mixture was subjected to an intermediate suspending treatment to agitate the mixture by a homomixer at a rotation rate of 10,000 rpm at a temperature of 40° C. or less for 30 minutes.

The resultant intermediate aqueous suspension was mixed with 3 parts by weight of a low molecular weight surfactant component consisting of 0.8 part by weight of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652 and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 at a temperature of 40° C. or less for 5 minutes.

A uniform aqueous suspension of composite particles including the calcium carbonate particles and having a particle size of 0.6 to 10 μm.

The resultant aqueous suspension was subjected to the same precipitation test as in Example 1 at a temperature of 50° C. for 30 days. As a result, the degree of precipitation was 1%. The precipitate was completely re-suspended by turning the cylinder upside down three times or less.

Example 8

One part by weight of a high molecular weight surfactant component consisting of a POE (polymerization degree=20)- POP (polymerization degree=70) block copolymer having an average molecular weight of 5897, 1 part by weight of POE (polymerization degree=14) styrylphenylether having a molecular weight of 1015, and 30 parts by weight of particulate DCMU having an average particle size of 50 μm were mixed into 58.3 parts by weight of water.

The resultant mixture was subjected to a first suspending treatment by agitating the mixture by a homomixer at a rotation rate of 10,000 at a temperature of 40° C. or less for 30 minutes.

Into the resultant first aqueous suspension, 1 part by weight of Pronal EX300, 0.4 part by weight of magnesium stearate, 1 part by weight of magnesium sulfate, 4 parts by weight of ethyleneglycol and 0.4 part by weight of Carplex were mixed.

The resultant mixture was subjected to an intermediate suspending treatment to agitate the mixture by a homomixer at a rotation rate of 10,000 rpm at a temperature of 40° C. or less for 30 minutes.

The resultant intermediate aqueous suspension was mixed with 2.9 parts by weight of a low molecular weight surfactant component consisting of 1.0 part by weight of a POE (polymerization degree=11) alkylarylether having a molecular weight of 705, 1.4 parts by weight of an alkylbenzene sulfonic acid salt having a molecular weight of 652 and 0.5 part by weight of a POE (polymerization degree=15) alkylether having a molecular weight of 846, and having an average molecular weight of 704.

The resultant mixture was subjected to a second suspending treatment in which the mixture was agitated by a homomixer at a rotation rate of 5,000 at a temperature of 40° C. or less for 5 minutes.

A uniform aqueous suspension of composite particles including the DCMU particles and having a particle size of 20 to 30 μm and an average particle size of 26 μm.

The resultant aqueous suspension was subjected to the same precipitation test as in Example 1 at a temperature of 50° C. for 30 days. As a result, the degree of precipitation was 5% or less. The precipitate was completely re-suspended by turning the cylinder upside down three times or less.

Example 9

One part by weight of a high molecular weight surfactant component consisting of a POE (polymerization degree=5)-POP (polymerization degree=30) block copolymer having an average molecular weight of 2917, 1 part by weight of POE (polymerization degree=14) styrylphenylether having a molecular weight of 1015, and 30 parts by weight of particulate acetyl salicylic acid (Aspirin, trademark) having a particle size of 20 to 30 μm were mixed into 58.2 parts by weight of water.

The resultant mixture was subjected to a first suspending treatment by agitating the mixture by a homomixer at a rotation rate of 10,000 at a temperature of 40° C. or less for 30 minutes.

Into the resultant first aqueous suspension, 1 part by weight of Pronal EX300, 0.4 part by weight of magnesium stearate, 1 part by weight of magnesium sulfate, 4 parts by weight of ethyleneglycol and 0.4 part by weight of Carplex were mixed.

The resultant mixture was subjected to an intermediate suspending treatment to agitate the mixture by a homomixer at a rotation rate of 10,000 rpm at a temperature of 40° C. or less for 30 minutes.

The resultant intermediate aqueous suspension was mixed with 3 parts by weight of a low molecular weight surfactant component consisting of 0.8 part by weight of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652 and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 at a temperature of 40° C. or less for 5 minutes.

A uniform aqueous suspension of composite particles including the Aspirin particles and having an average particle size of 20 to 30 μm.

The resultant aqueous suspension was subjected to the same precipitation test as in Example 1 at a temperature of 50° C. for 30 days. As a result, the degree of precipitation was 5% or less. The precipitate was completely re-suspended by turning the cylinder upside down three times or less.

Example 10

One part by weight of a high molecular weight surfactant component consisting of a POE (polymerization degree=5)-POP (polymerization degree=30) block copolymer having an average molecular weight of 2917, 1 part by weight of POE (polymerization degree=14) styrylphenylether having a molecular weight of 1015, and 30 parts by weight of particulate carbon black (trademark: Carbon Black #556IK85, made by Shiraishi Calcium K. K.) having an average particle size of 0.25 μm were mixed into 58.2 parts by weight of water.

The resultant mixture was subjected to a first suspending treatment by agitating the mixture by a homomixer at a rotation rate of 10,000 at a temperature of 40° C. or less for 30 minutes.

Into the resultant first aqueous suspension, 1 part by weight of Pronal EX300, 0.4 part by weight of magnesium stearate, 1 part by weight of magnesium sulfate, 4 parts by weight of ethyleneglycol and 0.4 part by weight of a shaping agent (Aerosil 200) were mixed.

The resultant mixture was subjected to an intermediate suspending treatment to agitate the mixture by a homomixer at a rotation rate of 10,000 rpm at a temperature of 40° C. or less for 30 minutes.

The resultant intermediate aqueous suspension was mixed with 3 parts by weight of a low molecular weight surfactant component consisting of 0.8 part by weight of a POE (polymerization degree=6) alkylarylether having a molecular weight of 485, 0.3 part by weight of a POE (polymerization degree=8) alkylarylether having a molecular weight of 573, 1.4 parts by weight of an alkylbenzene sulfonic acid salt having a molecular weight of 652 and 0.5 part by weight of a POE (polymerization degree=6) alkylether having a molecular weight of 450, and having an average molecular weight of 566.

The resultant mixture was subjected to a second suspending treatment in which the mixture was agitated by a homomixer at a rotation rate of 5,000 at a temperature of 40° C. or less for 5 minutes.

A uniform aqueous suspension of composite particles including the carbon black particles and having an average particle size of 0.32 μm.

The resultant aqueous suspension was subjected to the same precipitation test as in Example 1 at a temperature of 50° C. for 30 days. As a result, the degree of precipitation was 5% or less. The precipitate was completely re-suspended by turning the cylinder upside down three times or less.

What we claimed is:

1. An aqueous suspension of composite particles, comprising:
   (A) an aqueous suspension medium, and
   (B) a plurality of composite particles suspended in the aqueous suspension medium, each of the composite particles comprising:
      (a) a core consisting of a solid or a liquid particle substantially insoluble or scantly soluble in the aqueous, suspension medium, and
      (b) a coating layer formed on the peripheral surface of the core particle and comprising
         (i) a high molecular weight surfactant component comprising at least one high molecular weight surfactant compound having an average molecular weight of 1100 or more and,
         (ii) a low molecular weight surfactant component comprising at least one low molecular weight surfactant compound having an average molecular weight of 1100 or loss and of at least 400 below the average molecular weight of the high molecular weight surfactant compound, wherein the core particles have an average particle size of 3 to 500 μm and the composite particles have an average particle size of 6 to 1000 μm.

2. The aqueous suspension as claimed in claim 1, wherein the core solid particles are selected from sustained release solid agricultural chemicals, white pigments, solid cosmetics, solid coloring materials, solid medicines and solid building materials in the form of fine particles, fibers, plates, sands or flakes.

3. The aqueous suspension as claimed in claim 1, wherein the core liquid particles comprises at least one member selected from liquid monomers and oligomers, liquid vehicles for paints, liquid food substances, liquid medicines, liquid cosmetic materials, and liquid agricultural chemicals.

4. The aqueous suspension as claimed in claim 1, wherein the high molecular weight surfactant compound is selected from:
   (1) salts of alkali metals, amines and ammonium with acrylic acid polymers,
   (2) copolymers of maleic anhydride with acrylic acid and salts of alkali metals, amines and ammonium with the copolymers,
   (3) copolymers of itaconic acid with acrylic acid and salts of alkali metals, amines and ammonium salts of the copolymers, (4) polyoxypropylene-polyoxyethylene block copolymers,
(5) copolymers of cationic monomers with nonionic monomers,
(6) sodium polystyrenesulfonate,
(7) melaminesulfonic acid-formaldehyde polycondensation products, and
(8) sodium salts of sulfonated-styrene-maleic anhydride copolymers
(9) Sodium salts of polyepoxysuccinic acid,
(10) Polycondensation products of sodium naphthalenesulfonate with formaldehyde,
(11) Polyvinyl alcohol,
(12) Dextrin-fatty acid esters,
(13) Carboxymethylcellulose,
(14) Ethylenediamine-POP.POE block polymers,
(15) Copolymers of alkylaminoalkyl(meth) acrylamides with (meth)acrylic acid alkylacrylamides or acrylonitrile,
(16) Graft copolymerization products of cationic derivatives of linear polysaccharides with olefin monomers, and
(17) Poly-4-vinylpyridine cationic surfactants.

5. The aqueous suspension as claimed in claim 1, wherein the low molecular weight surfactant component comprises at least one member selected from one of the group consisting of nonionic surfactant compounds, the group consisting of anionic surfactant compounds, the group consisting of cationic surfactant compounds, the group consisting of mixtures of at least one nonionic surfactant compound and at least one anionic surfactant compound, and the group consisting of mixtures of at least one nonionic surfactant compound and at least one cationic surfactant compound.

6. The aqueous suspension as claimed in claim 1, wherein the high molecular weight surfactant component has an average molecular weight of 1800 to 1,000,000 and the low molecular weight surfactant component has an average molecular weight of 100 to 1100.

7. The aqueous suspension as claimed in claim 1, wherein the coating layer on the core particle has an inner coating layer formed on the peripheral surface of the core particle and comprising the high molecular weight surfactant component and an outer coating layer formed on the inner coating layer and comprising the low molecular weight surfactant component.

8. The aqueous suspension as claimed in claim 1, wherein the coating layer further comprises a suspension stabilizer comprising at least one member selected from inorganic and organic water-soluble salts.

9. The aqueous suspension as claimed in claim 8, wherein the water-soluble salts are selected from water-soluble salts of alkali metals, alkaline earth metals and ammonia with sulfuric acid, nitric acid, phosphoric acid, hydrochloric acid and acetic acid.

10. The aqueous suspension as claimed in claim 7, wherein the outer coating layer further comprises a suspension stabilizer comprising at least one member selected from inorganic and organic water-soluble salts.

11. The aqueous suspension as claimed in claim 10, wherein the suspension stabilizer is distributed in an interface between the inner coating layer and the outer coating layer.

12. The aqueous suspension as claimed in claim 1, wherein the core particles are present in an amount of 0.1 to 75% by weight based on the total weight of the aqueous suspension.

13. The aqueous suspension as claimed in claim 1, wherein the high and low molecular weight surfactant components are present in a total amount of 0.2 to 30% by weight based on the total weight of the aqueous suspension.

14. The aqueous suspension as claimed in claim 1, wherein the high molecular weight surfactant component is present in an amount of 0.1 to 5% by weight based on the total weight of the aqueous suspension.

15. The aqueous suspension as claimed in claim 8 or 10, wherein the suspension-stabilizer is present in an amount of 0.1 to 30% by weight based on the total weight of the aqueous suspension.

16. A process for producing an aqueous suspension of composite particles comprising:
    subjecting a particulate solid substance or a liquid substance to a suspending treatment in an aqueous treating liquid comprising an aqueous suspension medium, a high molecular weight surfactant component comprising at least one high molecular weight surfactant compound having an average molecular weight of 1100 or more, and a low molecular weight surfactant component comprising at least one low molecular weight surfactant compound having an average molecular weight of 1100 or less and at least 400 below the average molecular weight of the high molecular weight surfactant compound, the particulate solid substance and the liquid substance being substantially insoluble or scantly soluble in the aqueous suspension medium, thereby to provide a plurality of composite particles suspended in the aqueous suspension medium, said composite particles having an average particle size of 6 to 1000 $\mu$m, and each comprising a core consisting of the solid or liquid particle, said core particles having an average particle size of 3 to 500 $\mu$m, and a coating layer formed on the peripheral surface of the core particle and comprising the high molecular weight surfactant component and the low molecular weight surfactant component.

17. The process as claimed in claim 16, wherein the suspending treatment includes:
    (a) a first suspending treatment in which the particulate solid substance or the liquid substance is firstly suspended in a first aqueous treating liquid containing the high molecular weight surfactant component to provide a first aqueous suspension; and
    (b) a second suspending treatment in which the low molecular weight surfactant component is admixed into the first aqueous suspension, and in the resultant admixture, the first suspended particles are secondly suspended to provide a second aqueous suspension, thereby to provide a coating layer having an inner coating layer formed on the peripheral surface of the core solid particle and comprising the high molecular weight surfactant component and an outer coating layer formed on the inner coating layer and comprising the low molecular weight surfactant component.

18. The process as claimed in claim 17, further comprising mixing, at a stage during or before the first suspending treatment, or between the first and second suspending treatments, or during or after the second suspending treatment, a suspension-stabilizer comprising at least one member selected from inorganic and organic water-soluble salts into the aqueous treating liquid, thereby to cause the stabilizer to be distributed in the interface between the inner coating layer and the outer coating layer of each composite particle.

19. The process as claimed in claim 18, wherein the particulate solid substance or the liquid substance is mixed into the first aqueous treating liquid containing the high molecular weight surfactant component, the resultant mixture is subjected to the first suspending treatment, the resultant first suspension is mixed with the aqueous suspension stabilizer, the resultant mixture is subjected to an intermediate suspending treatment; the resultant intermediate suspension is mixed with the low molecular weight surfactant component, and the resultant mixture is subjected to the second suspending treatment, to provide an aqueous suspension of the composite particles.

20. The process as claimed in claim 18, wherein the particulate solid substance or the liquid substance is subjected to a pre-suspending treatment in an aqueous treating liquid containing the suspension stabilizer; the resultant aqueous pre-suspension is mixed with the high molecular weight surfactant component; the resultant mixture is subjected to the first suspending treatment; the resultant first aqueous suspension is mixed with the low molecular weight surfactant component; and the resultant mixture is subjected to the second suspending treatment, to provide the aqueous suspension of the composite particles.

21. The process as claimed in claim 18, wherein the particulate solid substance or the liquid substance is subjected to the first suspending treatment in the aqueous treating liquid comprising the high molecular weight surfactant component; the resultant first aqueous suspension is mixed with the low molecular weight surfactant component; the resultant mixture is subjected to the second suspending treatment; and the resultant second aqueous suspension is mixed with the suspension stabilizer, to provide an aqueous suspension of the composite particles.

22. The process as claimed in any of claims 16 to 21, wherein each suspending treatment is carried out by agitating the aqueous treating liquid containing the particulate solid substance or the liquid substance with an agitator at a revolution rate of 3000 to 15000 rpm at a temperature lower than the boiling temperature of the aqueous treating liquid.

* * * * *

UNITED STATES PATENT AND TRADEMARK OFFICE
CERTIFICATE OF CORRECTION

PATENT NO.        : 5,889,088
DATED             : March 30, 1999
INVENTOR(S)       : KISUNO et al.

It is certified that error appears in the above-identified patent and that said Letters Patent is hereby corrected as shown below:

On the title page, item
Please change

[73]    Assignee: "Kawasaki-sho, Japan" to --Kawasaki-shi, Japan--.

Signed and Sealed this

Fourteenth Day of March, 2000

Attest:

Q. TODD DICKINSON

Attesting Officer

Commissioner of Patents and Trademarks